(12) United States Patent
Stergiopulos

(10) Patent No.: US 7,128,750 B1
(45) Date of Patent: Oct. 31, 2006

(54) FLOW CONTROL METHOD AND DEVICE

(75) Inventor: Nikos Stergiopulos, St-Sulpice (CH)

(73) Assignee: Endoart S.A., La Rippe (CH)

( * ) Notice: Subject to any disclaimer, the term of this patent is extended or adjusted under 35 U.S.C. 154(b) by 647 days.

(21) Appl. No.: 10/031,469

(22) PCT Filed: Jul. 19, 2000

(86) PCT No.: PCT/EP00/06907

§ 371 (c)(1),
(2), (4) Date: May 29, 2002

(87) PCT Pub. No.: WO01/05463

PCT Pub. Date: Jan. 25, 2001

(30) Foreign Application Priority Data

Jul. 19, 1999 (EP) .................................. 99305689

(51) Int. Cl.
*A61B 17/08* (2006.01)
(52) U.S. Cl. ..................................... 606/158; 606/157
(58) Field of Classification Search ................ 606/157, 606/158; 600/16–18
See application file for complete search history.

(56) References Cited

U.S. PATENT DOCUMENTS

| 3,538,917 A | 11/1970 | Selker |
| 3,749,098 A | 7/1973 | DeBennetot |
| 3,750,194 A | 8/1973 | Summers |
| 3,810,259 A | 5/1974 | Summers |
| 3,863,622 A | 2/1975 | Buuck |
| 4,118,805 A | 10/1978 | Reimels |
| 4,146,029 A | 3/1979 | Ellinwood, Jr. |
| 4,256,093 A | 3/1981 | Helms et al. |
| 4,256,094 A | 3/1981 | Kapp et al. |
| 4,828,544 A | 5/1989 | Lane et al. |
| 5,509,888 A | 4/1996 | Miller |
| 5,571,121 A | 11/1996 | Heifetz |
| 5,662,711 A * | 9/1997 | Douglas ........................ 604/9 |
| 5,704,893 A | 1/1998 | Timm |
| 5,769,877 A | 6/1998 | Barreras, Sr. |
| 5,771,903 A | 6/1998 | Jakobsson |
| 5,847,447 A | 12/1998 | Rozin et al. |
| 5,879,320 A | 3/1999 | Cazenave |
| 5,938,669 A | 8/1999 | Klaiber et al. |
| 6,470,892 B1 * | 10/2002 | Forsell ..................... 623/23.65 |
| 6,531,964 B1 | 3/2003 | Loving |

FOREIGN PATENT DOCUMENTS

| DE | 40 37 043 | 5/1992 |
| DE | 44 27 583 | 2/1996 |
| DE | 195 08 129 | 9/1996 |
| GB | 1174814 | 12/1969 |
| WO | WO9601597 | 1/1996 |
| WO | WO 88/00455 | 1/1998 |
| WO | WO9963907 | 12/1999 |
| WO | WO0009047 | 2/2000 |

(Continued)

*Primary Examiner*—Eduardo C. Robert
*Assistant Examiner*—Jessica R. Baxter
(74) *Attorney, Agent, or Firm*—Luce, Forward, Hamilton & Scripps LLP; Nicola A. Pisano, Esq.

(57) ABSTRACT

An arterio-venous graft (16) is provided with a constriction device (20) near its arterial end. The constriction device (20) is used to reduce the flow through the AV graft under normal conditions and to relieve the constriction when high flow through the AV graft is required, such as for vascular access for hemodialysis.

39 Claims, 8 Drawing Sheets

FOREIGN PATENT DOCUMENTS

| | | |
|---|---|---|
| WO | WO0009048 | 2/2000 |
| WO | WO0015158 | 3/2000 |

* cited by examiner

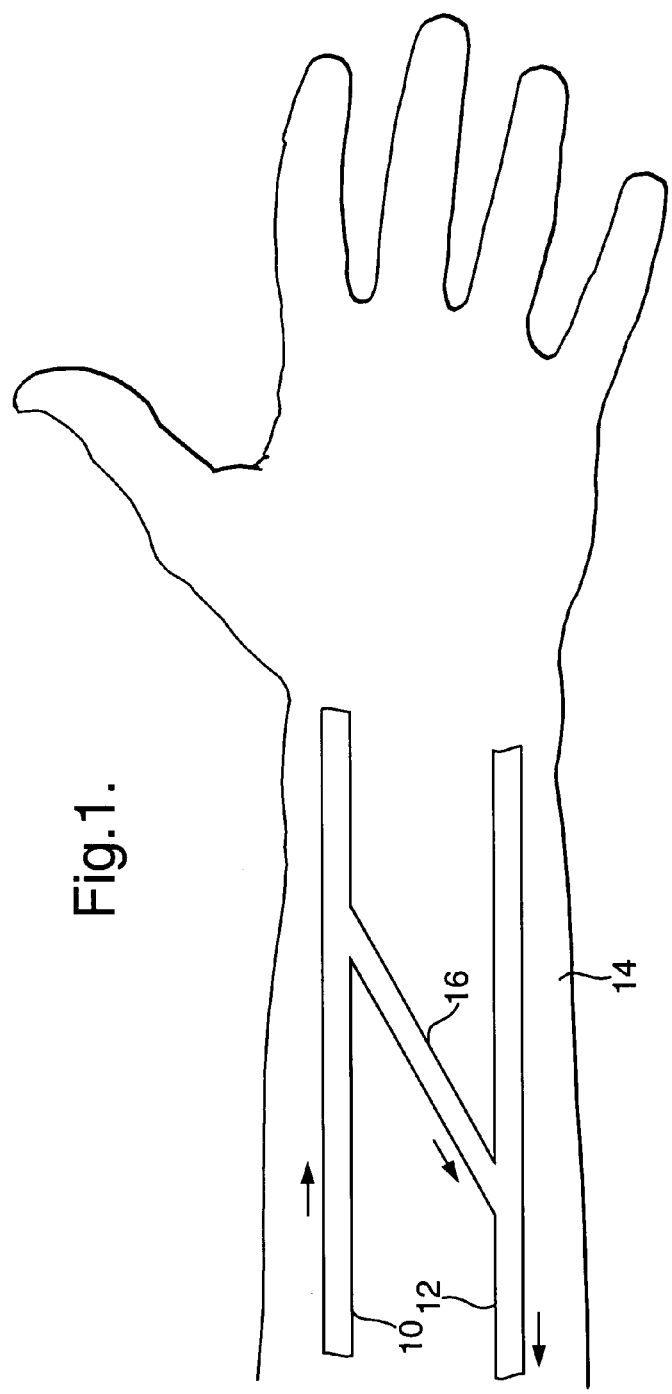
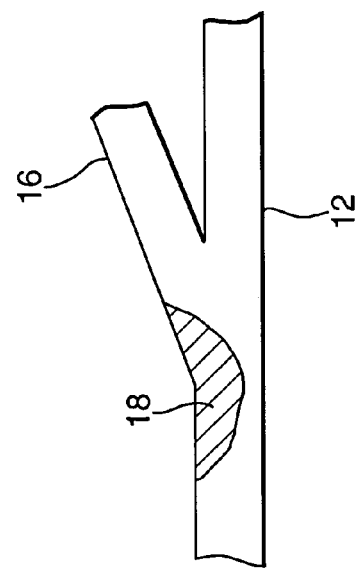

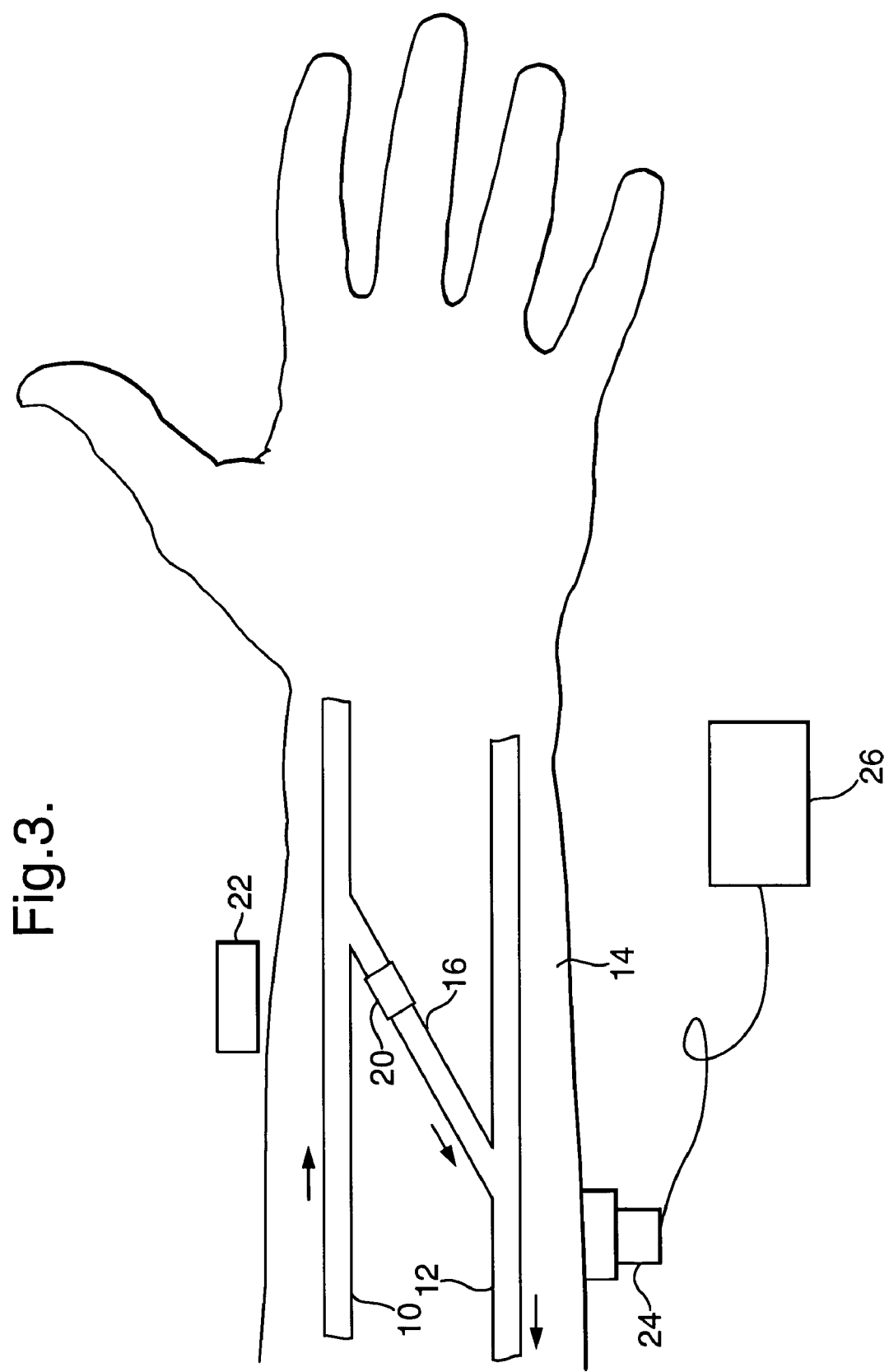

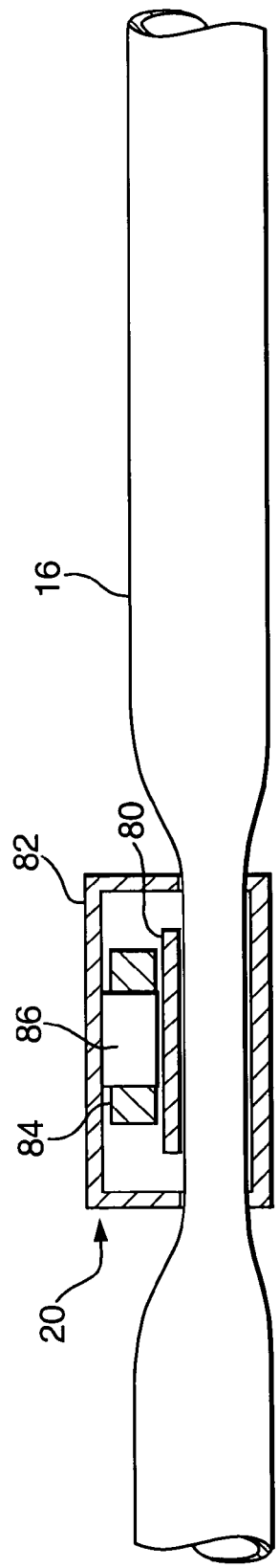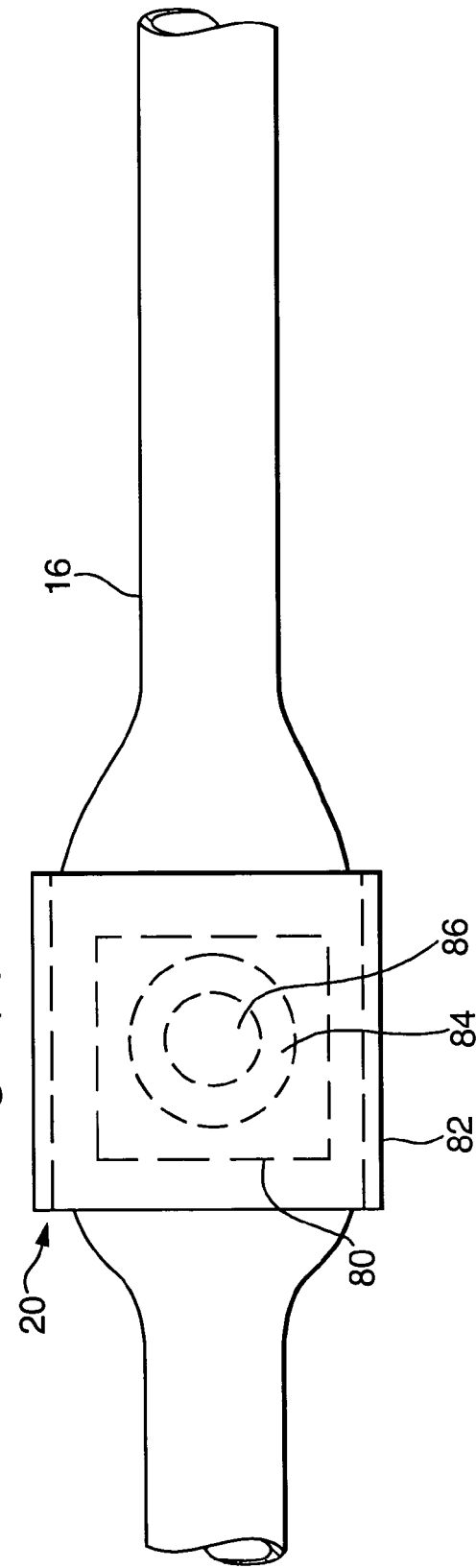

FLOW CONTROL METHOD AND DEVICE

This invention relates to a method of flow control of a bodily vessel, for example for use in an arterio-venous graft, hereinafter referred to as an AV graft. The invention also relates to a device for controlling flow in a bodily vessel, such as an AV graft, and a combination of such a device and a graft.

Patients with kidney disease, particularly those with end stage renal disease (ESRD), require hemodialysis in order to remove metabolites and the like from their blood stream. This can be a very time-consuming process, but the time can be lessened by providing a large blood flow to the hemodialysis machine. Even though this is done, hemodialysis can still take about four hours and is needed about three times a week.

In order to provide high blood flow to and from the hemodialysis machine, vascular access with high blood flow is needed. One method of providing this is illustrated in FIG. 1. An artery 10 and a vein 12 are located in the arm 14 of the patient. A vessel 16, known as an AV graft or shunt, is grafted to connect the artery 10 and vein 12. As the AV graft 16 is a direct connection between the artery 10 and vein 12 and has a relatively large cross-sectional area, a high flow through it occurs. The direction of flow is indicated by the arrows in FIG. 1. Catheters (not shown) can be connected to the AV graft 16, when hemodialysis is required. The catheters can tap into the high flow through the AV graft 16 to provide a high flow to and from the hemodialysis machine.

However, there are also considerable problems with this technique. One of these, illustrated in FIG. 2, is that stenosis occurs at the outflow tract where the AV graft 16 is connected to the vein 12, that is at the venous anastomosis side of the graft. The stenosis 18 is an unnatural narrowing of the vessel, and if unopened by angioplasty, the stenosis progresses until the vein is completely blocked. The stenosis is due to neo-intimal hyperplasia, that is the response of the vessel to the abnormal conditions. Various mechanisms are considered as possibly contributing to the stenosis development. The flow through the vein is typically 10 to 20 times higher than normal. This leads to turbulence and flow separation such that the flow is not smooth or laminar, and the stenosis develops as a result. Another factor is that the vein is exposed to a higher blood pressure than normal, because it is directly connected to the artery. The blood pressure in an artery is typically 100 mm Hg, whereas the blood pressure in a vein is typically 5 mm Hg. The vein tends to arterialise in response to this, for example by thickening of the vein wall and this may contribute to the stenosis. A further possible factor is that, in the presence of the graft, the flow in the vein is pulsatile. There is a significant compliance mismatch between the AV graft, which, if synthetic, is quasi-rigid, and the vein which is compliant. The pulsatile flow produces an oscillating stress concentration at the junction, i.e. suture line, between the AV graft 16 and the vein 12. Although the suture usually does not fail, the stenosis may be in response to the oscillating stress concentrated at the junction.

This is a considerable problem. In 90% of AV grafts, stenosis develops at the venous anastomosis side. AV graft survival is around only 1.5 years. Conventionally, alleviation of this problem requires surgery, such as angioplasty to remove the stenosis or surgery to implant a new AV graft in a different limb of the patient.

A further problem is that the AV graft 16 effectively provides a short circuit between the artery 10 and vein 12 and the high flow through the AV graft 16 requires a huge additional cardiac output. Normal cardiac output is typically 5 liters per minute, but with the AV graft in place this can increase to 7 liters per minute. This large additional cardiac output can be very problematic indeed, and can result in fatal cardiac failure for about 5% of AV graft patients.

According to the present invention there is provided a method of flow control in a AV graft or AV fistula used for vascular access for an extracorporeal circuit, said method comprising the steps of:

(a) applying partial constriction to a vessel to provide a reduced flow through said AV graft or AV fistula, when flow through said extracorporeal circuit is not occurring; and;

(b) changing the degree of constriction, to modify the flow through the AV graft or AV fistula, when flow through said extracorporeal circuit is to occur.

Applying partial constriction can reduce or eliminate turbulence, and lower the blood pressure in the vein. The constriction can also act as a strong wave reflector to reduce or eliminate the pulsatile flow at the venous anastomosis. All of these can alleviate stenosis, prolong the life of the AV graft or AV fistula and reduce the necessary cardiac output. Changing the degree of constriction when flow through said extracorporeal circuit is to occur enables a high flow to be provided for vascular access.

The constriction of the vessel is only partial, preferably to maintain a reduced but significant residual flow through the AV graft to avoid thrombosis, and to keep the vein matured and able to handle the high flow when necessary.

Preferably the constriction is applied over an elongate portion of the vessel. This enables the flow control to be achieved by viscous dissipation in favour of turbulent dissipation.

Preferably the constriction is applied at a plurality of positions along the vessel and/or the profile of the constriction is controlled along its length. This enables turbulence caused by the constriction to be minimised.

Preferably the constriction reduces the cross-sectional area of the lumen of the vessel, but maintains the length of the perimeter thereof, again to favour viscous dissipation.

Preferably, when applying the constriction to the vessel, the flow at the venous anastomosis of the AV graft or AV fistula is monitored so that when constricted, the flow is maintained at a level below the onset of turbulence.

Preferably the vessel is an AV graft.

Preferably the constricting step comprises constricting said AV graft at its arterial end. This enables any turbulence caused by the constriction to subside before the blood flow reaches the venous anastomosis.

The invention provides a device for controlling flow in an AV graft or AV fistula used for vascular access for an extracorporeal circuit, said device comprising:

a) means for applying partial constriction to a vessel, to provide a reduced flow through said AV graft or Av fistula, when flow through said extracorporeal circuit is to occur, and b) means for changing the degree of constriction, to modify the flow through the AV graft or AV fistula, when flow through said extracorporeal circuit is to occur.

The invention also provides a device, for controlling flow in a bodily vessel, said device comprising an actuator for releasably constricting said bodily vessel; and a rotatable member for driving said actuator.

Preferably the rotatable member comprises a drive shaft of a motor or comprises a rotor rotatable by an externally applied magnetic field.

Preferably the motor is an electrical micromotor.

The invention also provides a device, for controlling flow in a bodily vessel, said device comprising a deformable member which is reversibly deformable by a change in temperature or magnetic field; and an actuator acted on by said deformable member for releasably constricting said bodily vessel, wherein said deformable member is deformable between a first state in which said actuator applies constriction to said bodily vessel, and a second state in which said actuator reduces said constriction of said bodily vessel.

Preferably the thermally deformable member comprises a shape-memory material or a liquid filled capsule.

Preferably the device of the invention further comprises an antenna for receiving signals for controlling the actuator. This avoids the need for access to the device through the skin and the potential risk of infection.

Preferably the device further comprises a converter for converting radio frequency energy received by the antenna into energy for powering the device to operate the actuator. This has the advantage of avoiding the need for an internal power source, such as a battery, in the device, and radio frequency activated devices are NMR-proof.

The invention further provides a device, for controlling flow in a bodily vessel, said device comprising an actuator for releasably constricting said bodily vessel, wherein said actuator comprises a clip having two constriction portions with an adjustable separation therebetween for accommodating said bodily vessel and a control portion for releasably holding said two constriction portions such that said separation is held at least one predetermined amount.

Preferably the constriction portions are integrally formed as one member which makes the device simple and cheap to fabricate.

Embodiments of the invention will now be described, by way of example only, with reference to the accompanying drawings, in which:

FIG. 1 is a schematic view of a human lower arm, illustrating a conventional AV graft in situ;

FIG. 2 is a close-up view of the venous anastomosis of FIG. 1, illustrating a problem associated with the AV graft of FIG. 1;

FIG. 3 is a schematic view of a human lower arm, illustrating an arrangement according to the present invention;

Figure 4A:
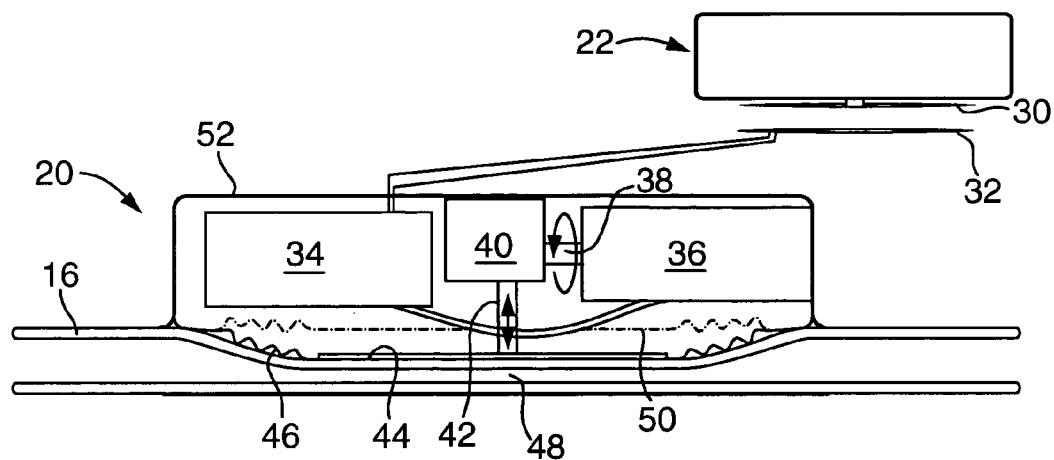
Figure 4B:
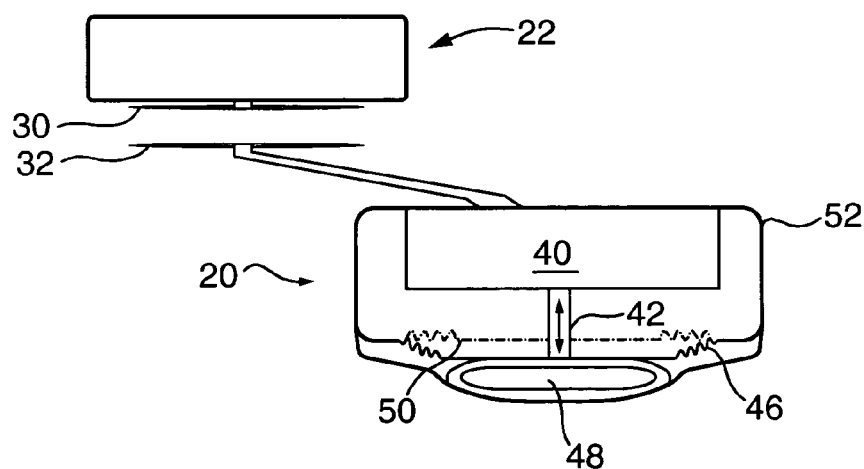
Figure 4C:
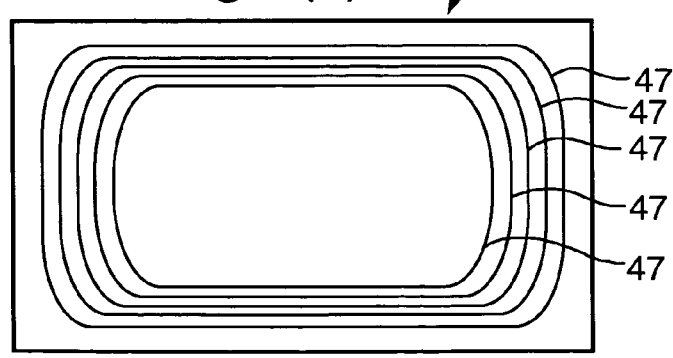
Figure 5:
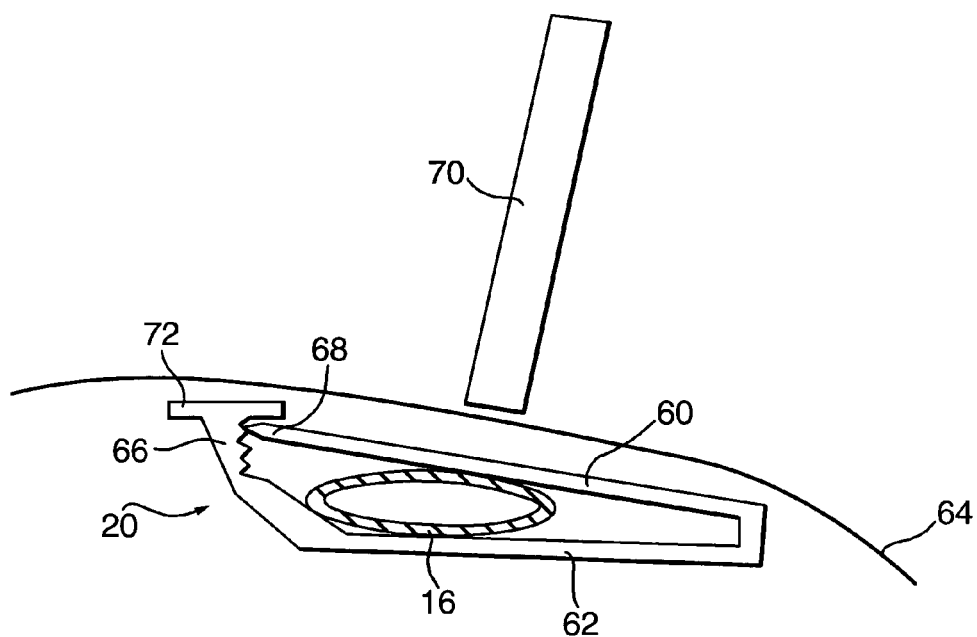
Figure 7:
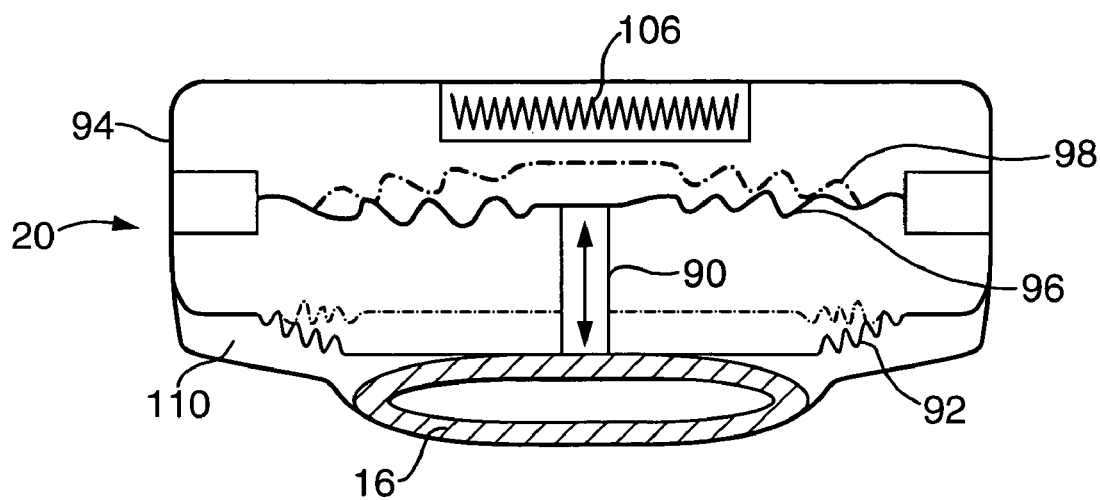
Figure 8:
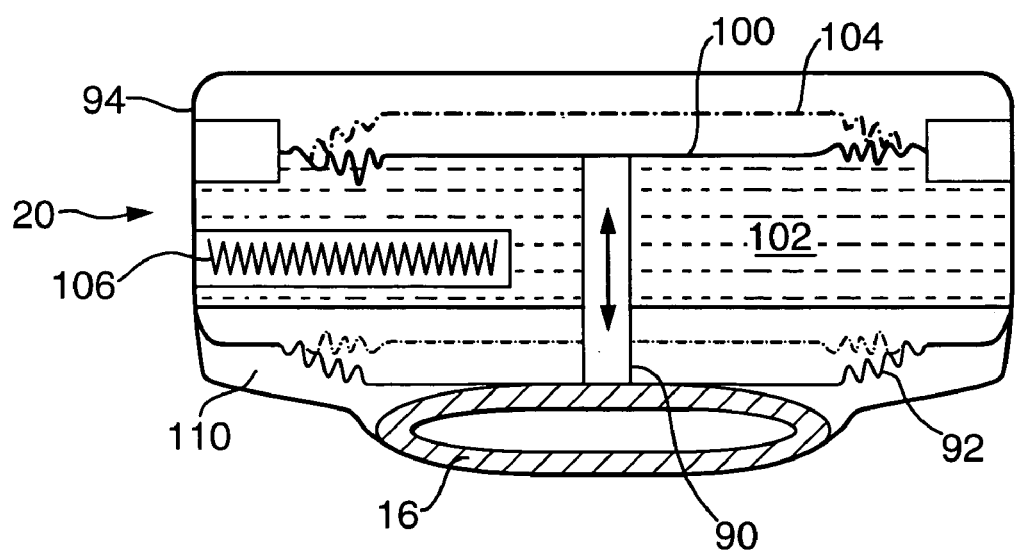
Figure 9:
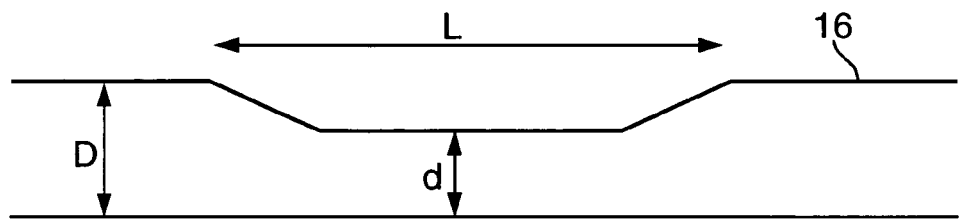
Figure 10:
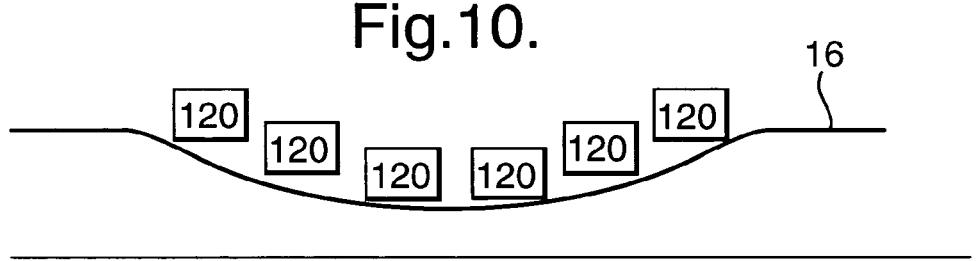
Figure 11:
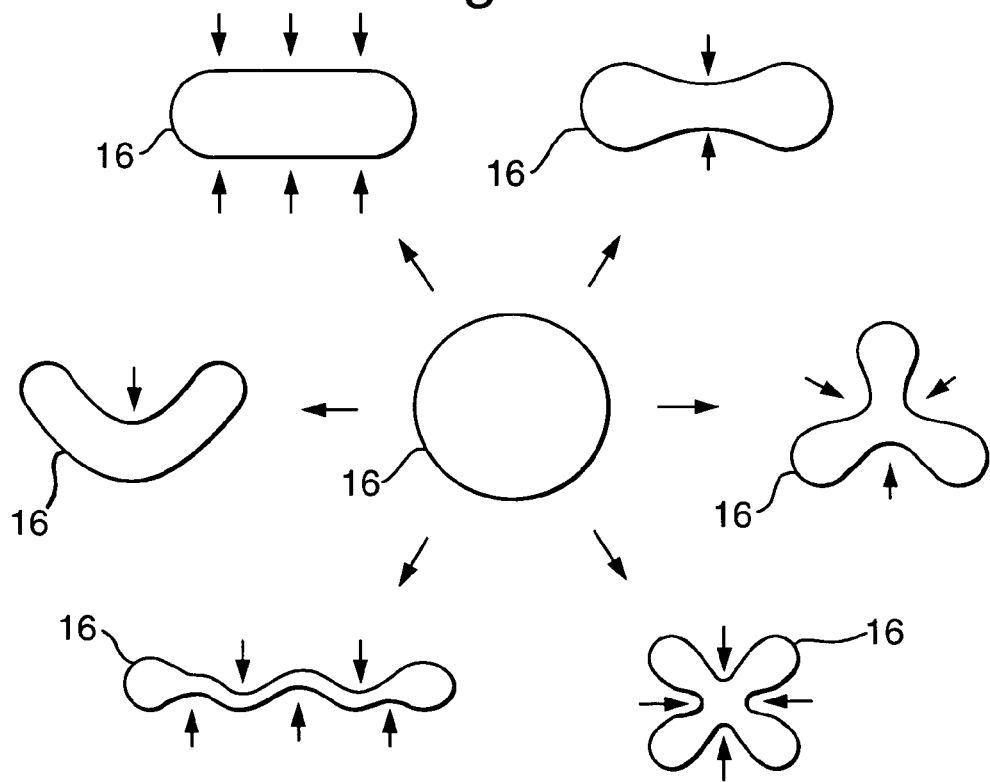
Figure 12:
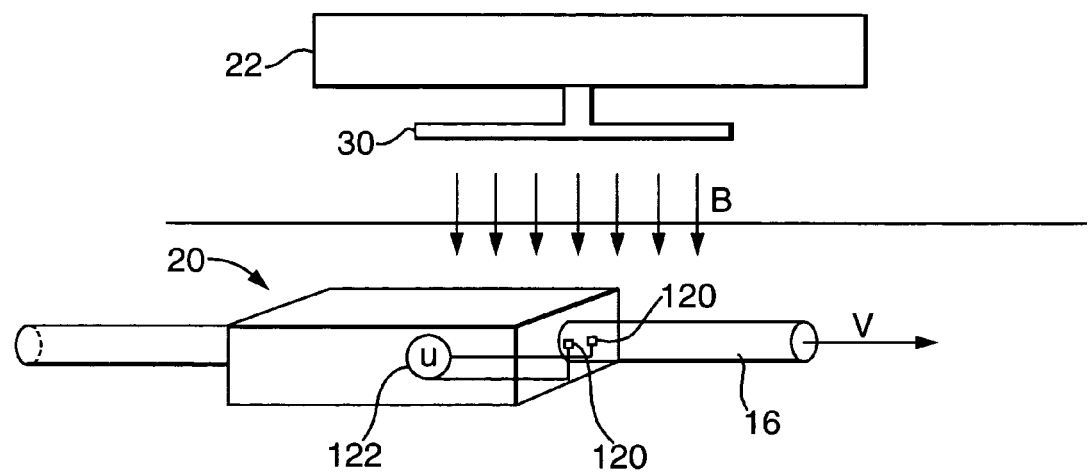
Figure 13:
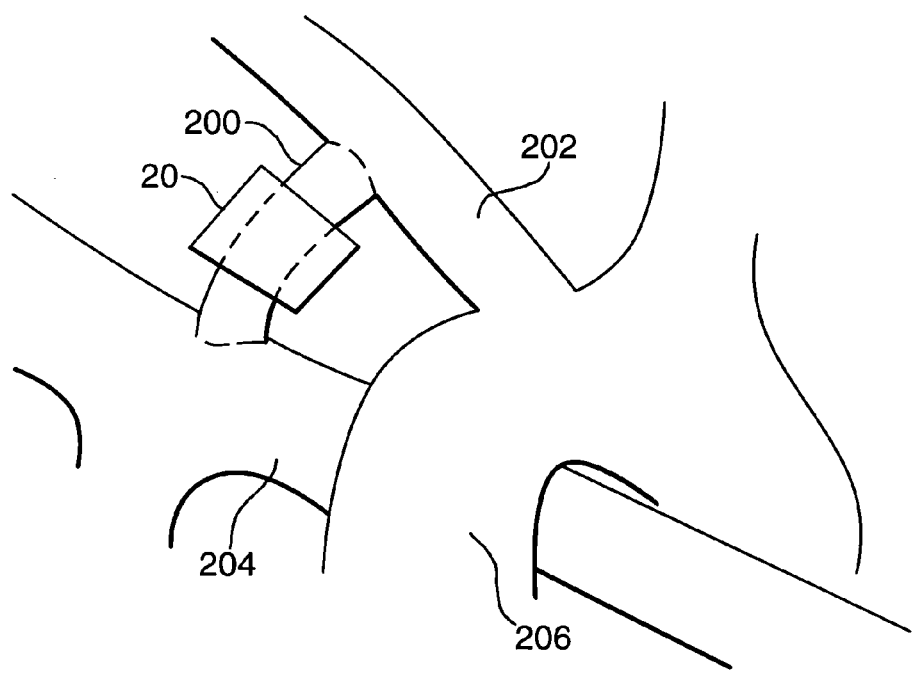

FIGS. 4(a) and 4(b) are schematic cross-sectional views of a first embodiment of apparatus according to the present invention, shown applied to an AV graft;

FIG. 4(c) is a plan view of a deflectable membrane of an embodiment of the invention;

FIG. 5 shows a second embodiment of an apparatus according to the present invention;

FIGS. 6(a) and 6(b) show a third embodiment of an apparatus according to the invention in cross-section and plan view, respectively;

FIGS. 7 and 8 show cross-sectional views of fourth and fifth embodiments of apparatus according to the invention;

FIGS. 9, 10 and 11 are explanatory diagrams for illustrating further aspects of the present invention;

FIG. 12 illustrates schematically an embodiment of the invention incorporating an electromagnetic flow measurement system; and FIG. 13 illustrates an application of the invention to a Blalock-Taussig shunt.

FIG. 3 shows an arrangement according to the present invention, with corresponding parts labelled the same as in FIG. 1. The AV graft 16 may be an artificial vessel, for example, made of PTFE or GORE-TEX™ or other synthetic material, or the AV graft may be an autologous graft. As illustrated in FIG. 3, the AV graft 16 is connected to an artery 10 and vein 12 in the arm 14 of the patient. However, the AV graft 16 may, of course, be located in other parts of the body, for example the leg, groin or neck.

A device 20 is provided for controlling blood flow in the AV graft 16. During the normal activities of the patient, the device 20 is used to constrict the AV graft 16 such that there is a reduced or residual flow therethrough. When flow through an extracorporeal circuit, such as a hemodialysis machine, is required, the degree of constriction is reduced, partially or fully, so that there is an increased, high flow through the AV graft 16. Catheters (not shown) can tap into the high flow in the AV graft 16 to provide high flow to and from a hemodialysis machine. The catheters may be upstream or downstream of the device 20 or may be provided on opposite sides of the device 20. A single catheter with a double lumen may also be used for flow to and from the AV graft 16.

As illustrated in FIG. 3, the constriction device 20 is used to constrict the AV graft 16 at its upstream end, in the vicinity of its connection with the artery 10. Preferably the constriction device 20 is wholly implanted within the patient and an external controller 22 is used telemetrically to control the constriction device 20.

When high flow through the AV graft 16 is no longer required, the constriction device 20 is used to re-apply constriction to reduce blood flow. A turbulence measuring device 24, 26 may be used to monitor turbulence in the vicinity of the venous anastomosis while the flow through the AV graft 16 is being reduced. As the degree of constriction is increased, the flow rate reduces such that a level will be reached at which turbulent flow substantially ceases to be detected by the turbulence measuring device. When this occurs, further change in constriction can be stopped and the flow maintained at that level below the onset of turbulence. Alternatively, the constriction may be increased until the turbulence has been diminished to a predetermined level, but not totally abolished. Preferably this diminished turbulence intensity is below the level at which stenosis may occur, but the flow rate is still sufficient to keep the vein matured. In this way an optimal quiescent flow can be established in the vicinity of the venous anastomosis side of the AV graft.

The turbulence measuring device 24, 26 can be a conventional Doppler device or a phonoangiographer and may advantageously be connected to the controller 22 or constriction device 20 automatically to control adjustment of the flow rate, or this may be done manually.

Further features of the method of the present invention will be apparent from the following description of devices according to the invention.

FIGS. 4(a) and 4(b) are longitudinal and transverse cross-sections, respectively, of a constriction device 20 and control device 22. The control device 22 has an antenna 30 for transmitting signals to an antenna 32 provided on the constriction device 20. The antennae 30, 32 are electromagnetically coupled to each other, but are of course on opposite sides of the skin (not shown) of the patient. A receiver 34 connected to antenna 32 sends electrical power to a motor 36 in response to the transmitted signal.

The constriction device 20 may contain an internal power source, such as a battery, which is controlled by the receiver 34 to deliver electrical power to the motor 36. Alternatively, the receiver 34 may comprise a radio frequency to DC converter and modulator, in which case radio frequency signals emitted by the antenna 30 are picked up by the antenna 32 and these signals are converted by the receiver 34 into electrical power to drive the motor 36, rather than the signals being used to control an internal power source of the device, thereby eliminating the need for batteries in the device which would need to be replaced periodically.

The motor 36 is a miniature motor, also known as a micro-machine, and when provided with electrical power it can be used to rotate a drive shaft 38 in either direction, or in one direction only, provided that the actuator performs a periodic displacement even if the micromotor shaft 38 always turns in the same direction. The dimensions of the micromotor 36 are sufficiently small to enable it to be encapsulated in an implantable enclosure, for example the motor may be 2 mm thick and 15 mm long. A rotary to linear transmission 40 converts the rotation of the drive shaft 38 into linear motion of an actuator comprising members 42, 44 and 46. Members 42 and 44 are rods or bars and member 46 is, for example, a fine titanium membrane that is in contact with the AV graft 16 or presses upon the AV graft through an intermediate material.

As shown in FIGS. 4(a) and 4(b), the actuator 42, 44, 46 is constricting the AV graft 16, such that the cross-sectional area of its lumen 48 is reduced. By sending appropriate signals, and through action of the motor 36, the constriction can be relieved by motion of the actuator, when high flow is required, and the position of the membrane 46 in this high flow state is indicated by the dashed line 50.

The constriction device 20 is encapsulated in an enclosure 52, such as a titanium or ceramic box, through which the AV graft can pass, or into which the AV graft can be slotted sideways. The antenna 32 as illustrated in FIGS. 4(a) and 4(b) is located outside the enclosure 52 so that it is not screened by the enclosure and to enable the antenna to be placed under the skin for optimal RF wave reception. This arrangement of having the antenna 32 external to and optionally remote from the enclosure 52 can be advantageous for cases in which the constriction device 20 is implanted deep within the body and the RF waves from the external control unit have a maximum penetration depth of 2 to 4 cm. Alternatively, for situations in which the constriction device 20 can be implanted just under the skin or not too deep, the antenna 32 can be internal, i.e. encapsulated within the enclosure 52 of the constriction device 20. In this alternative embodiment, the enclosure 52 or at least part of the enclosure 52 is non-metallic, for example ceramic or plastic to avoid screening of the RF waves. Having the antenna internal or integral to the enclosure 52 of the constriction device 20 is advantageous in simplifying the implantation of the device within the body.

The device may optionally include a sensor, not shown, such as a sensor for measuring the position of the actuator or for counting the number of revolutions of the drive shaft 3S. Sensors for measuring flow, turbulence or pressure may also be included. Information from the sensor(s) can then be transmitted from the constriction device 20 to the control device 22 via the antennae 30, 32, so that the controller 22 can control the constriction more precisely.

FIG. 5 illustrates an alternative constriction device 20 in the form of a clip. The actuator of the device comprises a pair of constriction portions 60, 62 separated by a gap through which the AV graft 16 passes. The separation between the constriction portions 60, 62 can be reduced by applying pressure to the skin 64 of the patient to constrict the AV graft 16. A control portion 66 comprises a series of grooves or notches engageable by an insertion portion 68 of the constriction portion 60. Pressure applied to the skin 64 moves the insertion portion 68 from the position shown in FIG. 5 into successively lower notches. When the required level of constriction is achieved, the engagement of the insertion portion 68 in the particular notch of the control portion 66 maintains that level of constriction.

A pressing device 70 may be used for this process and may comprise a sensor that detects the motion of the insertion portion 68 from one notch to the next so that the position of the constriction portions is known and an optimal level of constriction applied.

When high flow through the AV graft 16 is required, the constriction can be reduced by again applying pressure to the skin of the patient, but this time by pressing on a release portion 72. This splays the control portion 66 so that the insertion 68 disengages from the notches and the opening between the constriction portions 60, 62 increases.

As shown in FIG. 5, the constriction device 20 is formed from a single piece, such as by moulding it from a biologically compatible plastics material. This makes it very simple and cheap to fabricate.

Another embodiment of the constriction device is shown in FIGS. 6(a) and 6(b). It comprises an actuator plate 80, within an enclosure 82, for squeezing on the AV graft 16. A rotor 84 is screwed onto a threaded shaft 86. The rotor 84 comprises a series of magnetic north and south poles alternating around the shaft 86. The rotor 84 can comprise any suitable magnetic material, such as ferrite.

Application of an alternating or rotating magnetic field from outside the patient can cause the rotor 84 to revolve about the axis of the shaft 86. The threaded engagement between the rotor 84 and shaft 86 causes the rotor 84 to translate in the axial direction of the shaft 86, the direction of translation depending on the sense of rotation of rotor. In this way the externally magnetic field can be used to move the rotor 84 along the shaft 86 to urge the actuator plate 80 against the AV graft 16 to apply constriction thereto, or to release pressure from the actuator plate 80 and reduce the constriction when high flow through the AV graft 16 is required.

FIGS. 7 and 8 show two further embodiments of the constriction device 20 of the invention which both operate thermally. Each device has an actuator comprising a movable member 90 and a flexible membrane 92 for constricting an AV graft 16, the device being housed in an enclosure 94.

In the embodiment of FIG. 7, the actuator member 90 is connected to a sheet 96 made of a heat-deformable material. This is shown in its normal state at body temperature whereby the AV graft 16 is constricted to reduce the quiescent flow therethrough. On raising the temperature of the sheet 96 it deforms into the shape indicated by the dashed line 98 thereby pulling on the actuator 90, 92 to reduce the constriction on the AV graft 16. The material of the sheet 96 may be a shape-memory material, such as a so-called smart metal, or it could be a bi-metallic strip or any other suitable material that deflects on changing temperature, or a shape memory material that is magnetically activated.

In the device of FIG. 8, the actuator member 90 is connected to a deformable membrane 100 which defines one surface of a liquid filled capsule 102 containing a liquid with a low boiling point, such as just above body temperature, for example around 39° C. Under normal conditions the capsule 102 contains liquid and the actuator 90, 92 squeezes the AV graph 16 to reduce blood flow. On increasing the temperature of the substance in the capsule 102 above its boiling point, at least some of the liquid vaporises which results in an overall increase in volume of the contents of the capsule 102. This expansion deflects the membrane 100 and a force is transmitted via the member 90 to lift the flexible membrane 92 to relieve the constriction of the AV graph 16. The position of the deformable membrane 100 when in this state is indicated by the dashed line 104.

The devices 20 shown in FIGS. 7 and 8 may be provided with an optional heater 106, such as an electrical resistance. When it is desired to increase the blood flow through the AV graft 16, electric current is passed through the heater 106 to raise the temperature of the sheet 96 or liquid filled capsule 102 to move the actuator as described above. The electrical current may be provided by a battery associated with the device and controlled by signals from an external controller as described with reference to FIGS. 4(a) and 4(b), or the electrical current may be provided by a radio frequency converter which converts radio frequency radiation into electrical power, without the need for an internal battery, as also described with reference to FIGS. 4(a) and 4(b). Alternatively, the increase in temperature necessary to change the state of the thermal device may be provided by an external heat source. This eliminates the need for the heater 106. The external heat source may take the form of, for example, an infrared lamp directed onto the skin in the vicinity of the device 20. The heater 106 could also be an antenna which heats up when an appropriate electromagnetic field is applied.

When high flow through the AV graft 16 is no longer required, such as when hemodialysis has been completed, power to the heater 106 is cut off, or the external heat source removed. The sheet 96 or fluid filled capsule 102 cools back to normal body temperature and returns to the configurations shown in FIGS. 7 and 8 in which the actuator 90, 92 is squeezing the AV graft 16.

All of the above described constriction devices are intended to be wholly implantable within the patient. The enclosures 52, 82, 94 comprise a titanium, ceramic or plastic box and the dimensions of the sides in transverse cross-section may be in the region of 10 to 30 mm, the unconstricted diameter of an AV graft being typically 5 to 8 mm. The flexible membrane 46, 92, in contact with the AV graft 16 may be a very thin (i.e. 20 to 60 µm thick) titanium sheet or a thicker titanium membrane preferably with appropriate corrugations 47 to facilitate deflection, as shown in plan view in FIG. 4(c). The corrugations can be seen in cross-section in FIGS. 4(a), 4(b), 7 and 8. The region surrounding the AV graft 16, but within the respective enclosure, such as the region 110 shown in FIGS. 7 and 8 may contain a deformable, but incompressible, material such as gel to control the constriction of the AV graft 16.

FIG. 9 shows schematically a constriction, such as in an AV graft 16. The normal diameter of the vessel is D, the constricted diameter is d, and the constriction is applied over a length L. It is preferred that the method and devices of the present invention apply the constriction over an elongate portion of the AV graft 16, for example as shown in FIG. 4(a). Preferably the length L is at least twice the original diameter D, and L may even be five to ten or more times the diameter D. The reasons for this are as follows. For a given flow rate Q through the AV graft 16, the viscous losses are proportional to LQ, whereas the turbulent losses are proportional to $[(D/d)^2-1]^2 Q^2$. These two losses contribute to the overall dissipation caused by the constriction which results in the pressure drop and reduced flow rate. An acute localised constriction produces much turbulence which can cause thrombosis or unwanted stenosis downstream at the venous anastomosis, or in the AV graft itself if it is made of living tissue. The same overall flow reduction can be achieved by increasing the length of the constriction to increase viscous loss, but reducing turbulent loss.

One way to increase the length of the constriction is to provide multiple constriction devices in series along the AV graft 16. Another method is to provide a single elongate actuator within the device or multiple actuators disposed along the length of the device.

FIG. 10 illustrates a further technique for reducing turbulence caused by the constriction, namely by controlling the profile of the constriction such that abrupt transitions in diameter are avoided. The profile of the constriction can be controlled by providing a plurality of actuators 120, each of which squeezes the AV graft 16 by a controlled amount. The actuators 120 may all be provided within a single constriction device, or each actuator 120 may be provided in a respective constriction device disposed in series along the AV graft 16. Alternatively, a single actuator of a predetermined profile may be used to cause a desired constriction profile.

A further technique for favouring viscous dissipation over turbulent dissipation is illustrated with reference to FIG. 11. A transverse cross-section of the unconstricted AV graft is approximately circular as shown in the centre of FIG. 11. Applying an isotopic force around the periphery to squeeze the vessel approximately equally in all directions would tend to reduce the cross-section of the vessel to be a circle of smaller diameter. However, viscous losses are related to the area of the wall of the vessel and hence to the perimeter of the cross-section. By squeezing the AV graft 16 unequally in different directions, the perimeter of the lumen can be maintained substantially constant in length while reducing its cross-sectional area. Various exemplary resulting shapes are shown in FIG. 11. The arrows illustrate the directions and points of application of the squeezing force. The devices according to the invention can achieve constrictions of these shapes by a variety of ways, such as having ridged actuators, or a plurality of actuators applying pressure in different directions or surrounding the AV graft 16 by a gel to control the shape of the deformation.

A further feature of the invention is to adhere the outer surface of the AV graft to the actuator using a glue. According to Bernoulli's equation, $p+\frac{1}{2}\rho v^2$ is constant, where p is pressure, $\rho$ is viscosity and v is flow velocity. At a constriction, the flow velocity increases to maintain throughput. At sufficiently high velocity, the pressure given by Bernoulli's equation can become lower than the external pressure on the vessel or even become negative. Thus, at a constriction it is possible for collapse of the vessel to occur because the reduced pressure sucks the walls inwards. The flow of course then stops and the vessel recovers, but vessel collapse is problematic and results in erratic flow conditions. Gluing the wall of the AV graft to the actuator prevents collapse by maintaining a minimum diameter of the AV graft, even when constricted. AV graft collapse may also be prevented if the constriction is appropriately shaped, as shown in some of the examples in FIG. 11, to resist further buckling under reduced pressure.

As previously mentioned, in one arrangement catheters for extracorporeal flow to and from the AV graft 16 may be provided on opposite sides of the device 20. In this case it can be beneficial to increase constriction of the graft during e.g. hemodialysis in order to augment flow through the extracorporeal machine. For the rest of the time, the constriction is still partially applied to alleviate the problems, such as caused by turbulence, whilst keeping the vein matured.

The method and device of the invention can also be used with AV fistulas, in which case the flow control device is placed on the artery or vein, just proximal or distal to the fistula, respectively.

A further preferred aspect of the invention, which can be used with any of the above-described embodiments, is to incorporate a flow-measuring device into the variable flow control device 20. FIG. 3 illustrated an external flow or turbulence measuring device 24, 26, however, according to the present further embodiment, the implanted device incorporates flow-measuring apparatus. The flow measured by the device may be communicated, for example, via an antenna 32, to an external device to give a reading of the flow passing through the AV graft. Alternatively, or in addition, the flow measurement may be used internally within the implanted device to control the constriction applied, using a feed-back loop, to regulate the flow.

Examples of two technologies that can be used in embodiments of the flow control device for measuring flow are described below.

(1) Ultrasonic Flow Measurements

A piezo-element emits ultrasound, which is reflected by the flowing blood, the reflected signals being slightly changed in frequency through the Doppler effect, thereby carrying information on velocity which is detected. Referring to FIG. 4(*a*) by way of illustrative example, the information on velocity is transmitted from the implanted device 20 via antenna 32 to the external antenna 30 and is then received and displayed by the external control unit 22.

(2) Electromagnetic Flow Sensor

The flowmeter according to this embodiment works on the principle of Faraday's Law of Induction, which states that if a conductor is moved within a magnetic field, a voltage is induced at right angles to the direction of movement in that conductor and at right angles to the magnetic field. The voltage generated is proportional to the average velocity of the moving conductor. The voltage signal U is proportional to the product vDB, where U=voltage across the channel, v=conductor average velocity, D=distance between the electrodes and B=magnetic flux density.

An example of this embodiment is illustrated in FIG. 12. The blood in the vessel 16 acts as the moving conductor. A magnetic field B can be applied by an external magnet. Preferably the magnetic field coming from the external antenna 30 is used. This is advantageous because it eliminates the need to instal magnets or other means of imposing a magnetic field. Preferably the magnetic field is alternating, in which case a different frequency of B is used than the one used for the control of the flow control device 20. Thus the external control unit 22 emits one frequency, for example, for the telemetric control of a motor 36 and for power generation, and another frequency for creating the magnetic field B required for the flow measurement.

The voltage measuring electrodes measuring 120 are placed perpendicular to B and v, and with a precisely known separation D. The EMF generated between the electrodes 120 is sensed by a voltage measuring device 122. For improved measurement sensitivity, the voltage measuring device 122 is tuned to the frequency of the externally applied magnetic field B. The electrodes 120 can be encapsulated either in the main box of the device 20 or in an auxiliary chamber next to the main box.

All of the preceding methods and devices according to the invention have been described in terms of application to an AV graft. However, as mentioned in the introduction, they can also be applied to the variable flow control of other bodily vessels, by which is meant a generally tubular structure that transports material in the body, such as a blood vessel, lymph vessel, vessel in the digestive tract, vessel in the urinary tract, vessel in the reproductive tract, and so on. The bodily vessel can be natural, or a graft, such as an autologous graft or a synthetic graft. Two further exemplary embodiments of applications other than to AV grafts will now be described.

(A) Hypoplastic Left (or Right) Heart Syndrome

In this condition, blood is supplied by only a single ventricle of the heart. Referring to FIG. 13, pulmonary circulation must often be assured by providing a shunt 200 connecting the subclavian or innominate artery 202 to the right or left pulmonary artery 204. This is also known as the modified Blalock-Taussig shunt. The shunt 200 itself is a vascular graft, such as a PTFE tube. Survival of the patent is often dependent on the optimal distribution of flow between the shunt 200 and the aorta 206.

According to the present invention, a variable flow control device 20 is placed on the shunt 200. The shunt 200 drives flow from the systemic circulation in the innominate artery 202 to the pulmonary circulation in the pulmonary artery 204. The variable flow control device 20 is, for example, according to any one of the above described devices. The flow control device 20 enables the flow in the shunt to be regulated and according to a method of the invention, the flow in the shunt is controlled to equilibrate the repartition of flow between the systemic and pulmonary circulation.

(B) Esophageal Banding or Replacement of the Esophagus Valve

The valve at the end of the esophagus connecting the esophageal tube to the stomach may fail, causing re-entry of food from the stomach to the esophagus and consequent discomfort to the patent. Also, for the treatment of obesity, sometimes a banding at the end of the esophagus may be surgically placed. The banding causes a localised restriction to the esophageal tube. Banding is not a precise procedure and is not adjustable without further abdominal surgery. According to the present invention, a variable flow control device, such as embodied above, is located on the esophagus to alleviate either of these problems. The degree of esophageal restriction can be easily controlled telemetrically to allow controlled passage of food into the stomach when required but to restrict it at other times or to prevent re-entry of food from the stomach into the esophagus.

Whilst specific embodiments of the invention have been described above, it will be appreciated that the invention may be practised otherwise than as described. The description is not intended to limit the invention.

The invention claimed is:

1. A device, for controlling flow in a bodily vessel, said device comprising:
    an implantable enclosure;
    an actuator disposed within the implantable enclosure, the actuator configured to engage and to adjustably constrict said bodily vessel, the actuator comprising a rotatable member coupled to a drive shaft of an electrical micromotor via a rotary to linear transmission,
    a receiver disposed within the implantable enclosure, the receiver operatively coupled to the actuator to selectively adjust a degree of constriction applied by the rotatable member responsive to a signal received from an external control; and
    an external control device configured to telemetrically supply a signal to the receiver to control operation of the actuator.

2. A device according to claim 1, further comprising an antenna coupled to the receiver for receiving signals from the external control device.

3. A device according to claim 2, wherein the receiver comprises a converter for converting radio frequency energy received by said antenna into energy for powering the electrical micromotor.

4. A device according to claim 2, further comprising a sensor for sensing the state of the actuator and transmitting a signal via said antenna indicative of said state.

5. A device according to claim 2, further comprising at least one sensor for sensing at least one of pressure, flow rate and turbulence and transmitting a corresponding signal via said antenna.

6. A device according to claim 5, wherein said sensor measures at least one of flow rate, turbulence and pressure.

7. A device according to claim 6, wherein said sensor comprises at least one of a Doppler device, a phonoangiographer and an electromagnetic flow sensor.

8. A device according to claim 1, further comprising a battery.

9. A device according to claim 1, wherein said actuator further comprises a flexible membrane for pressing on said bodily vessel.

10. A device according to claim 9, wherein said membrane comprises at least one corrugation.

11. A device according to claim 1, wherein said actuator is arranged to constrict said bodily vessel non-uniformly around its transverse cross-sectional periphery.

12. A device according to claim 1, wherein said actuator is shaped to define a predetermined profile for said constriction.

13. A device according to claim 1, further comprising a plurality of said actuators.

14. A device according to claim 13, wherein the plurality of said actuators are arranged to constrict said bodily vessel along an elongate portion thereof.

15. A device according to claim 14 wherein the plurality of said actuators control the profile of the constriction along its length.

16. A device according to claim 13 wherein the plurality of said actuators control the profile of the constriction around the transverse cross-sectional periphery of said vessel.

17. A device according to claim 1, wherein the implantable enclosure comprising a titanium or ceramic implantable enclosure.

18. The device according to claim 1, and further comprising an implantable bodily vessel graft.

19. The device according to claim 18, wherein said actuator is adhered to said graft to prevent uncontrolled constriction of said graft.

20. The device according to claim 19, wherein said constriction is shaped to resist further buckling under reduced pressure.

21. The device according to claim 18, wherein said actuator is positioned at the upstream end of said graft.

22. The device according to claim 18, further comprising a deformable, but substantially incompressible, medium at least partially surrounding said graft at the location of said actuator.

23. The device according to claim 18, comprising a plurality of said devices disposed along said graft.

24. The device according to claim 18, wherein one end of said graft is connected to an artery and the other end of said graft is connected to one of an artery and a vein.

25. A device according to claim 1, further comprising a measuring device coupled to the drive shaft to count a number of revolutions of the drive shaft.

26. A device according to claim 25, wherein said measuring device further is configured to transmit a signal via said antenna to the external control device indicative of a state of the drive shaft.

27. A device according to claim 1, wherein said bodily vessel is one selected from the group consisting of a blood vessel, lymph vessel, vessel in the digestive tract, vessel in the urinary tract, vessel in the reproductive tract, an AV graft, an artery, a vein, a blood circulatory system shunt, a Blalock-Taussig shunt, and an esophagus.

28. A device according to claim 1, wherein said actuator is configured to squeeze said vessel by applying force at one or more points around its periphery in a non-uniform manner.

29. A device according to claim 1, wherein said actuator is configured to maintain substantially constant the length of the perimeter of said vessel in transverse cross-section, whilst adjusting the cross-sectional area of the lumen of said vessel.

30. A device according to claim 1, wherein said actuator is configured to maintain constriction at a level such that a flow rate through the vessel is below onset of turbulence.

31. The device according to claim 1 wherein the device is configured for use in the treatment of kidney disease.

32. The device according to claim 1 wherein the device is configured for use in hemodialysis.

33. The device according to claim 1 wherein the device is configured for use in the treatment of hypoplastic heart syndrome.

34. The device according to claim 1 wherein the device is configured for use in the treatment of esophagus valve failure.

35. The device according to claim 1 wherein the device is configured for use in the treatment of obesity.

36. A method of flow control in an AV graft, comprising:
providing an implantable enclosure housing an actuator configured to engage and to adjustably constrict said AV graft, the actuator comprising a rotatable member coupled to a drive shaft of an electrical micromotor via a rotary to linear transmission, a receiver disposed within the implantable enclosure and operatively coupled to said actuator to selectively adjust a degree of constriction applied by the rotatable member responsive to a signal received from an external control;
providing an external control device configured to telemetrically supply a signal to the receiver to control operation of the actuator;
implanting the implantable enclosure so that the actuator engages said AV graft; and
operating the external control device to selectively constrict said AV graft at its arterial end.

37. A method according to claim 36, wherein the external control devices is operated so that said actuator applies constriction over an elongate portion of said AV graft.

38. A method according to claim 36, wherein the external control devices is operated so that said actuator constricts the AV graft at a plurality of positions along said AV graft.

39. A method according to claim 36, wherein the external control devices is operated so that said actuator constricts said AV graft so as to reduce the cross-sectional area of the lumen of said AV graft at said constriction while substantially maintaining the length of the perimeter of said AV graft.

* * * * *